United States Patent
Habu et al.

(10) Patent No.: US 6,176,832 B1
(45) Date of Patent: Jan. 23, 2001

(54) CARDIOVASCULAR INFORMATION MEASUREMENT SYSTEM

(75) Inventors: Yoshiyuki Habu; Mitsutoshi Yaegashi, both of Nakai-machi (JP)

(73) Assignee: Terumo Kabushiki Kaisha, Tokyo (JP)

( * ) Notice: Under 35 U.S.C. 154(b), the term of this patent shall be extended for 0 days.

(21) Appl. No.: 09/141,263

(22) Filed: Aug. 27, 1998

(30) Foreign Application Priority Data

Sep. 1, 1997 (JP) .................................................. 9-236363

(51) Int. Cl.[7] ........................................................ A61B 5/02
(52) U.S. Cl. ........................ 600/485; 600/490; 600/500; 600/503
(58) Field of Search ..................................... 600/485, 490, 600/493–6, 500, 503, 504, 505, 465

(56) References Cited

U.S. PATENT DOCUMENTS

| 5,099,852 | 3/1992 | Meister et al. . |
| 5,105,817 | 4/1992 | Uchibori et al. . |
| 5,309,916 | 5/1994 | Hatschek . |
| 5,411,028 | * 5/1995 | Bonnefous .......................... 600/465 |
| 5,453,575 | * 9/1995 | O'Donnell, Jr. ..................... 600/465 |
| 5,535,747 | 7/1996 | Katakura . |
| 5,588,438 | 12/1996 | Weng et al. . |
| 5,671,750 | 9/1997 | Shinoda . |
| 5,967,987 | * 10/1999 | Sumanaweera et al. ............ 600/454 |

FOREIGN PATENT DOCUMENTS

| 1 905 620 | 8/1970 | (DE) . |
| 4-250135 | 9/1992 | (JP) . |
| 4-329938 | 11/1992 | (JP) . |
| 5-56971 | 3/1993 | (JP) . |
| 7-241288 | 9/1995 | (JP) . |
| 8-215156 | 8/1996 | (JP) . |

* cited by examiner

Primary Examiner—Robert L. Nasser
(74) Attorney, Agent, or Firm—Burns, Doane, Swecker & Mathis, LLP

(57) ABSTRACT

It is an object of the present invention to provide a cardiovascular information measurement system capable of performing an accurate blood pressure measurement and calculating an accurate cardiovascular index in consideration of the pulsation of a blood vessel wall. To achieve this object, the cardiovascular information measurement system includes ultrasonic transducer groups (4a, 4b) for simultaneously detecting sectional shapes (3a, 3b) of two arterial portions, a cross-sectional area calculation unit (5) for calculating cross-sectional areas of the two arterial portions on the basis of the detected sectional shapes, a flow velocity calculation unit (6) for calculating an average blood flow velocity in an artery on the basis of the cross-sectional areas calculated by the cross-sectional area calculation unit (5), a pulse wave velocity calculation unit (7) for calculating a pulse wave propagation velocity between the two arterial portions in accordance with time changes in the detected sectional shapes of the two arterial portions, a relative blood pressure calculation unit (8) for calculating a relative blood pressure value to a reference blood pressure value obtained in a specific time phase, on the basis of the calculated blood flow velocity and the calculated pulse wave propagation velocity, and an absolute blood pressure calculation unit (10) for calculating an absolute blood pressure value on the basis of the relative blood pressure value and the reference blood pressure value obtained in the specific time phase and measured in advance.

18 Claims, 11 Drawing Sheets

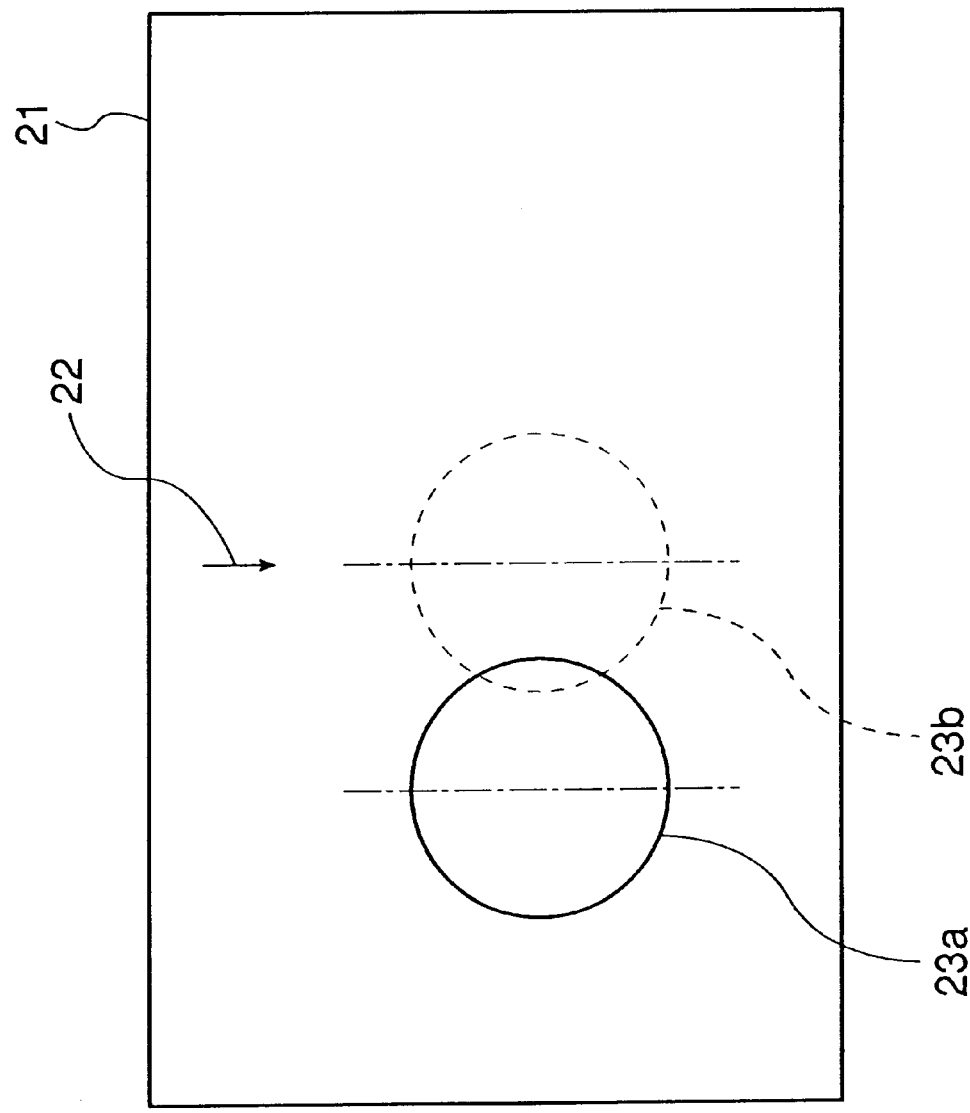

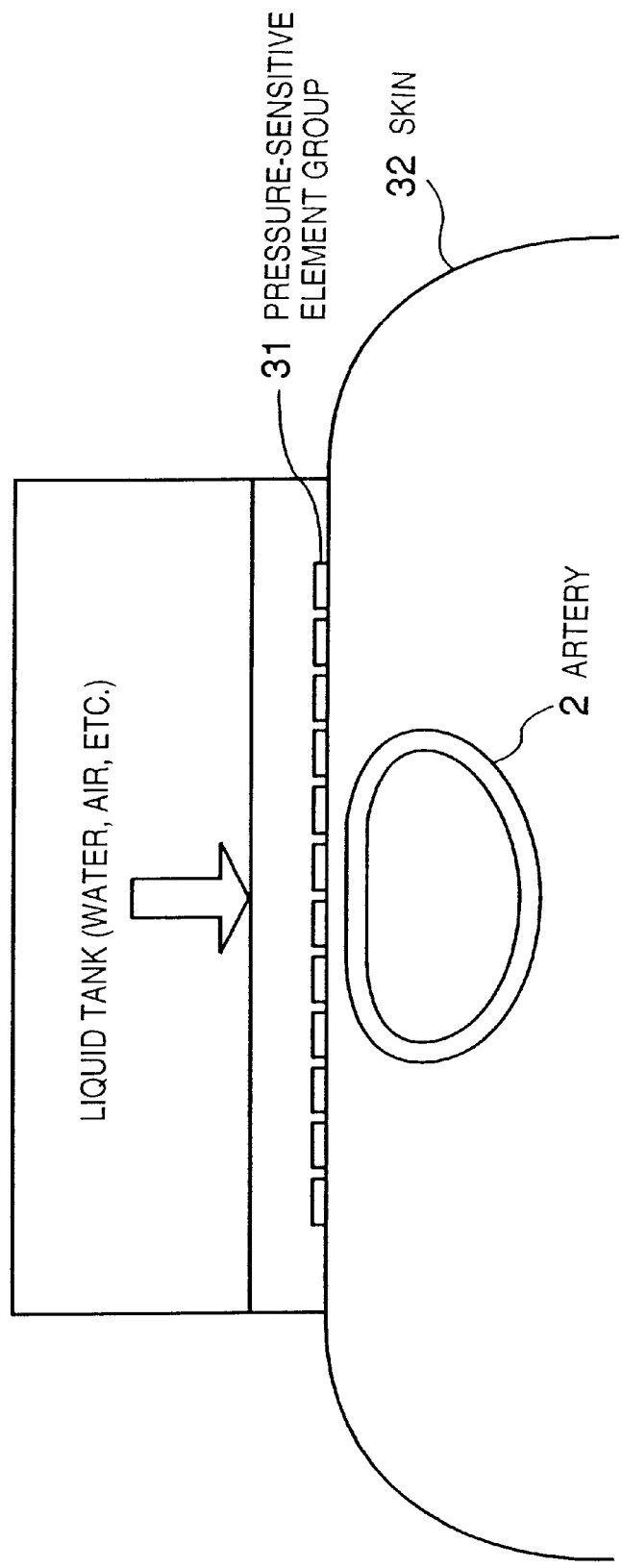

34a

34b

CARDIOVASCULAR INFORMATION MEASUREMENT SYSTEM

BACKGROUND OF THE INVENTION

1. Field of the Invention

The present invention relates to a cardiovascular information measurement system capable of noninvasively and continuously measuring vital cardiovascular information.

2. Description of the Related Art

Various indices such as a volume flow of blood, viscoelasticity caused by vasodilation and vasoconstriction are conventionally used as cardiovascular indices for grasping the states of circulatory organs of a patient.

A volume flow of blood is measured by the following method. The blood vessel of a patient is irradiated with an ultrasonic wave, the blood flow velocity is obtained using a Doppler signal generated by the blood flow. The volume flow of blood is then obtained in accordance with the relationship between the blood flow velocity and the cross-sectional area of the blood vessel.

An optical flow method for measuring a velocity vector using the liminance gradient of continuous image data is used as a method of obtaining vasodilation and vasoconstriction rates.

When the volume flow of blood is to be obtained from the blood flow velocity calculated using the Doppler signal, demand has arisen for a technique for easily and continuously calculating the cross-sectional area of the blood vessel of interest in order to obtain the volume flow of blood.

The above optical flow method undesirably requires complicated sequential calculations.

A method of winding a manchette on an arm portion of a patient and measuring the blood pressure from the resultant vibration or sound has been practiced as a conventional method of measuring the blood pressure. However, when the blood pressure must be measured for several days upon surgical operation, the arm portion of the patient must be pressurized to result in considerable mental and physical loads.

To solve this problem, a method of measuring, with an ultrasonic wave, the propagation velocity of a pulse wave propagating through the blood vessel and measuring the blood pressure is disclosed in Japanese Patent Laid-Open No. 7-241288. According to this method, the blood pressure is calculated using the following theoretical expression:

$$\Delta P = \rho C \Delta v$$

where
- $\Delta P$: the pressure change
- $\rho$: the blood density
- $\Delta v$: the flow velocity change
- $C$: the pulse wave velocity This theoretical expression is disclosed in the following reference (edited by The Japan Hydraulics & Pnuematics Society, New Hydropneumatic Handbook, Section 1, Chapter 3, 24–25, OHM-sha, Ltd., 1988). However, this theoretical expression is an expression based on a condition that no change occurs in the blood vessel wall. That is, this expression is made in no consideration of the influence of the blood vessel wall.

SUMMARY OF THE INVENTION

The present invention, therefore, has been made in consideration of the conventional problems described above, and has as its object to provide a cardiovascular information measurement system capable of noninvasively measuring the cross sectional shape of a blood vessel and calculating a cardiovascular index based on the measured sectional shape.

It is another object of the present invention to provide a cardiovascular information measurement system capable of noninvasively measuring the sectional shape of a blood vessel and accurately measuring the blood pressure in consideration of the pulse wave of the blood vessel wall.

In order to solve the above problems and achieve the above objects, a cardiovascular information measurement system according to the first aspect of the present invention has the following arrangement.

That is, a cardiovascular information measurement system comprises sectional shape detection means for simultaneously detecting sectional shapes of at least two arterial portions, cross-sectional area calculation means for calculating cross-sectional areas of the two arterial portions on the basis of the sectional shapes detected by the sectional shape detection means, flow velocity calculation means for calculating an average blood flow velocity in an artery on the basis of the cross-sectional areas calculated by the cross-sectional area calculation means, pulse wave velocity calculation means for calculating a pulse wave propagation velocity between the two arterial portions in accordance with time changes in the sectional shapes of the two arterial portions which are detected by the sectional shape detection means, relative blood pressure calculation means for calculating a relative blood pressure value to a reference blood pressure value obtained in a specific time phase, on the basis of the blood flow velocity calculated by the flow velocity calculation means and the pulse wave velocity calculated by the pulse wave velocity calculation means, and absolute blood pressure calculation means for calculating an absolute blood pressure value on the basis of the relative blood pressure value and the reference blood pressure value obtained in the specific time phase and measured in advance.

A cardiovascular information measurement system according to the second aspect of the present invention has the following arrangement.

That is, a cardiovascular information measurement system comprises ultrasonic emission means for emitting an ultrasonic wave toward a blood vessel, ultrasonic wave detection means for detecting an ultrasonic wave reflected in a living body, binarization means for setting an appropriate threshold value in accordance with an angle between an incident direction of the ultrasonic wave and a blood vessel wall and binarizing an output signal from the ultrasonic detection means, and index calculation means for calculating a cardiovascular index on the basis of blood vessel sectional shape information obtained from information binarized by the binarization means.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

BRIEF DESCRIPTION OF THE DRAWINGS

FIG. 8 is a view showing a unit for detecting a position right above a blood vessel;

FIG. 10 is a view showing the schematic arrangement of a pressure-sensitive element group for obtaining the pulse wave velocity;

DETAILED DESCRIPTION OF THE PREFERRED EMBODIMENTS

The preferred embodiments of the present invention will be described in detail with reference to the accompanying drawings.

(First Embodiment)

Figure 1:
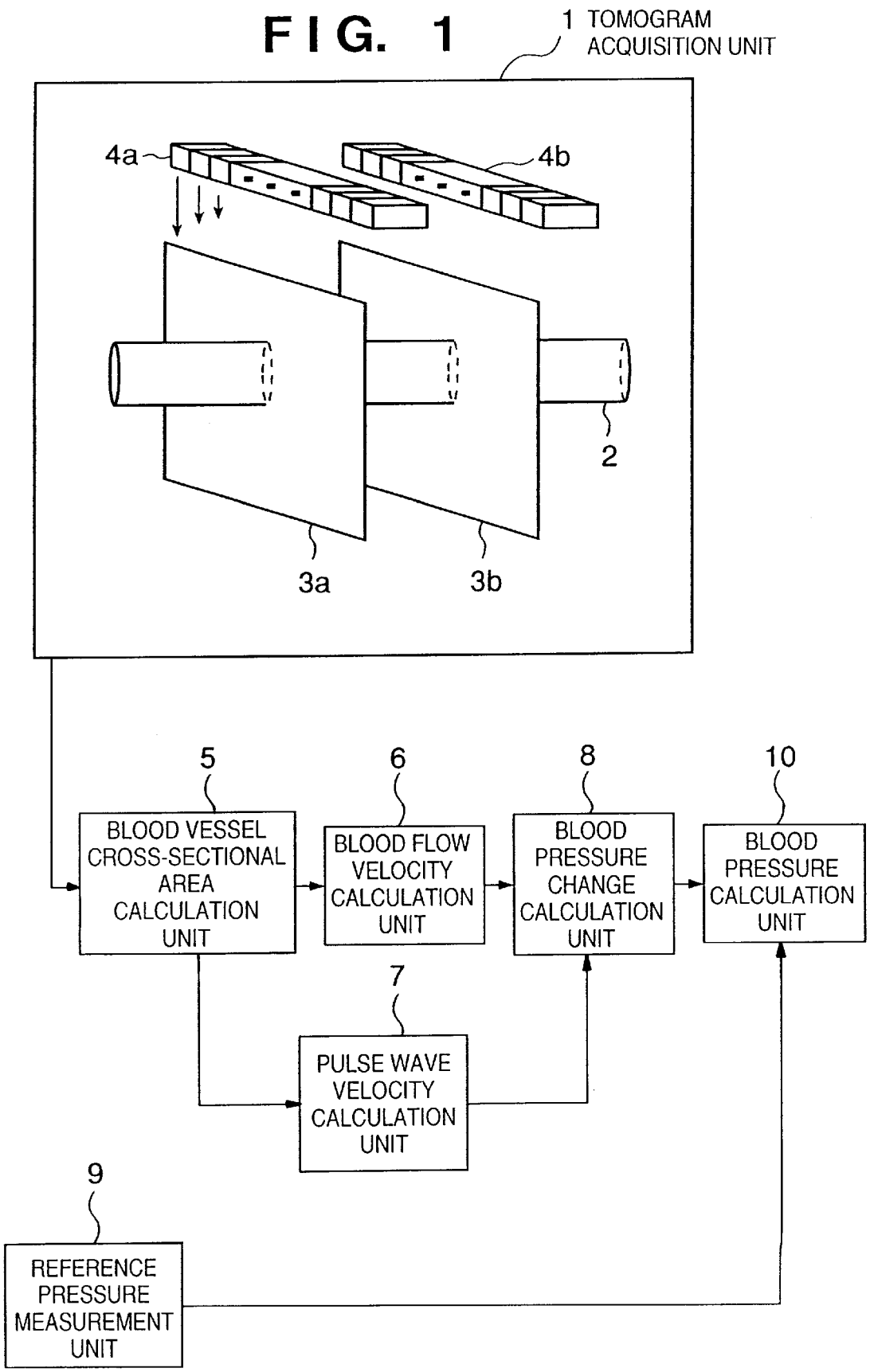
FIG. 1 is a diagram showing the arrangement of a blood pressure measurement apparatus as the first embodiment of a cardiovascular information measurement system of the present invention.

FIG. 1 is a diagram showing the arrangement of a blood pressure measurement apparatus as the first embodiment of a cardiovascular information measurement system according to the present invention.

As shown in FIG. 1, a tomogram acquisition unit 1 comprises ultrasonic transducer groups 4a and 4b for acquiring ultrasonic tomograms 3a and 3b of two adjacent points of one blood vessel. The acquired tomograms 3a and 3b are transmitted to a blood vessel cross-sectional area calculation unit 5 to extract the sections of the blood vessel. The blood vessel cross-sectional areas calculated by the blood vessel cross-sectional area calculation unit 5 are transmitted to a blood flow velocity calculation unit 6 and a pulse wave velocity calculation unit 7. The blood flow velocity calculation unit 6 calculates a blood flow velocity from the cross-sectional areas and the distance between the two points. The pulse wave velocity detection unit 7 calculates a pulse wave propagation velocity in accordance with the phase difference of a time change in cross-sectional areas between the two points. The blood flow velocity calculated by the blood flow velocity calculation unit 6 and the pulse wave velocity calculated by the pulse wave velocity calculation unit 7 are transmitted and substituted into the following conversion equation:

$$P - P0 = \rho C0 v + (1/8)\rho v^2$$

where

P: the blood pressure

P0 = minimum blood pressure (diastolic pressure)

$\rho$: the specific gravity of the blood

C0: the telediastolic pulse wave propagation velocity v: the flow velocity averaged over cross-section of the blood vessel By the above equation, the relative value to the minimum blood pressure as the reference value is calculated and output to a blood pressure change calculation unit 8. The absolute value of the blood pressure at a given time point measured by a reference pressure measurement unit 9 is transmitted to a blood pressure calculation unit 10. The blood pressure calculation unit 10 continuously calculates blood pressure values.

Figure 2:
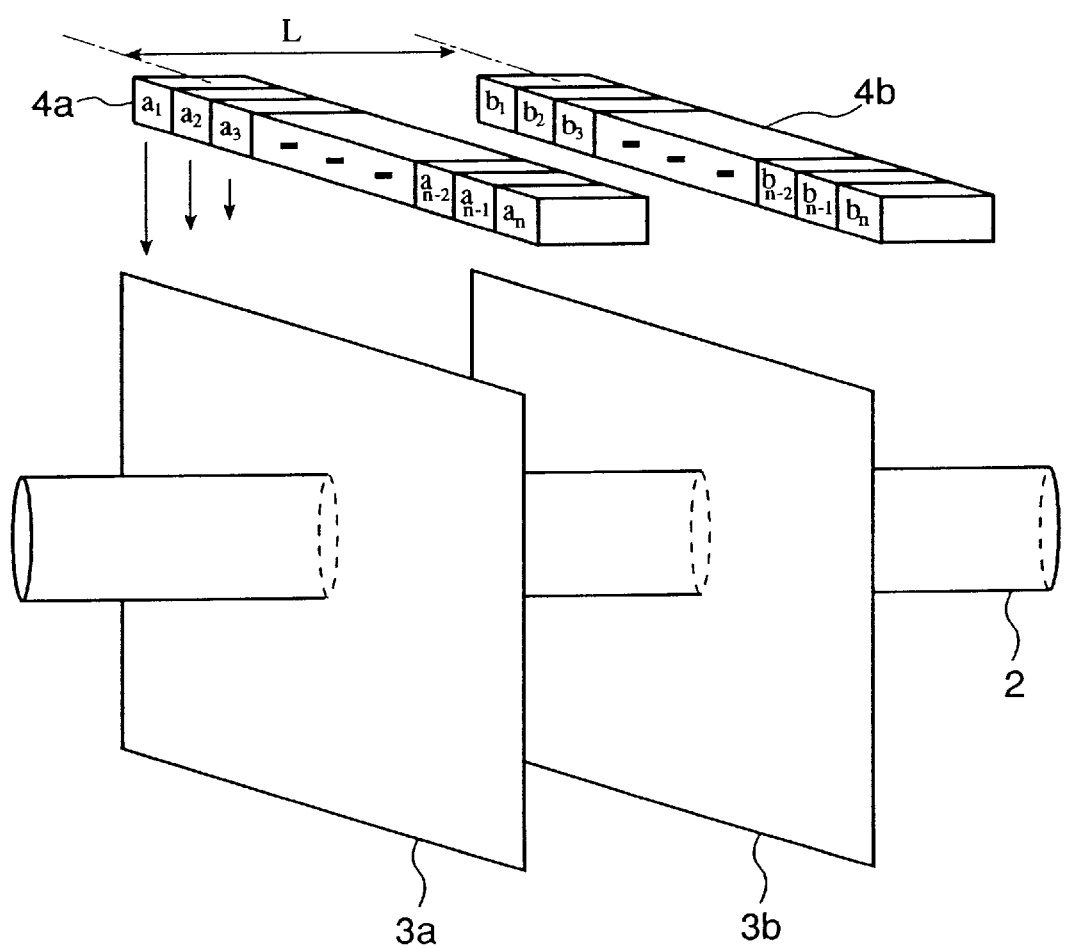
FIG. 2 is a perspective view showing the arrangement of a tomogram acquisition unit.

FIG. 2 shows the arrangement of a tomogram acquisition unit. The ultrasonic transducer group 4a comprises n (n is a natural number) ultrasonic transducers a1 to an, and the ultrasonic transducer group 4b comprises n ultrasonic transducers b1 to bn. The ultrasonic transducer group 4a is arranged parallel to the ultrasonic transducer group 4b and spaced apart from the group 4b by a distance L. The ultrasonic transducer a1 of the ultrasonic transducer group 4a emits an ultrasonic wave toward an artery 2 and detects a signal obtained upon reflecting the emitted ultrasonic wave by the arterial wall. This series of operations are repeated from the vibrator a1 to the vibrator an to obtain an ultrasonic tomogram 3a. After the arterial tomogram 3a is obtained, an arterial tomogram 3b is obtained by the same operation as in the operation of obtaining the arterial tomogram 3a.

For the sake of simplicity, the ultrasonic transducers perform transmission and reception one by one in an order of a1, a2, . . . , an to obtain tomograms. However, as in a general ultrasonic diagnosis apparatus, it is possible to obtain tomograms by beam forming using a plurality of vibrators. "Beam forming" is to form an ultrasonic beam having a target property by controlling the phase or delay distribution in the array.

An arbitrary method of acquiring arterial tomograms can be used as far as the arterial tomograms are obtained. In this embodiment, after the tomograms are obtained by the ultrasonic transducer group 4a, the tomograms are obtained by the ultrasonic transducer group 4b. The tomograms may be simultaneously obtained if they can be acquired. The conditions such as the tomogram acquisition order, the number of vibrator groups, and the shapes of tomograms can be arbitrarily set, as a matter of course. The conditions such as the number of ultrasonic transducers constituting each ultrasonic transducer group, the layout, the size, and the emission frequency can be set at any values within the scope of the present invention.

Figure 3:
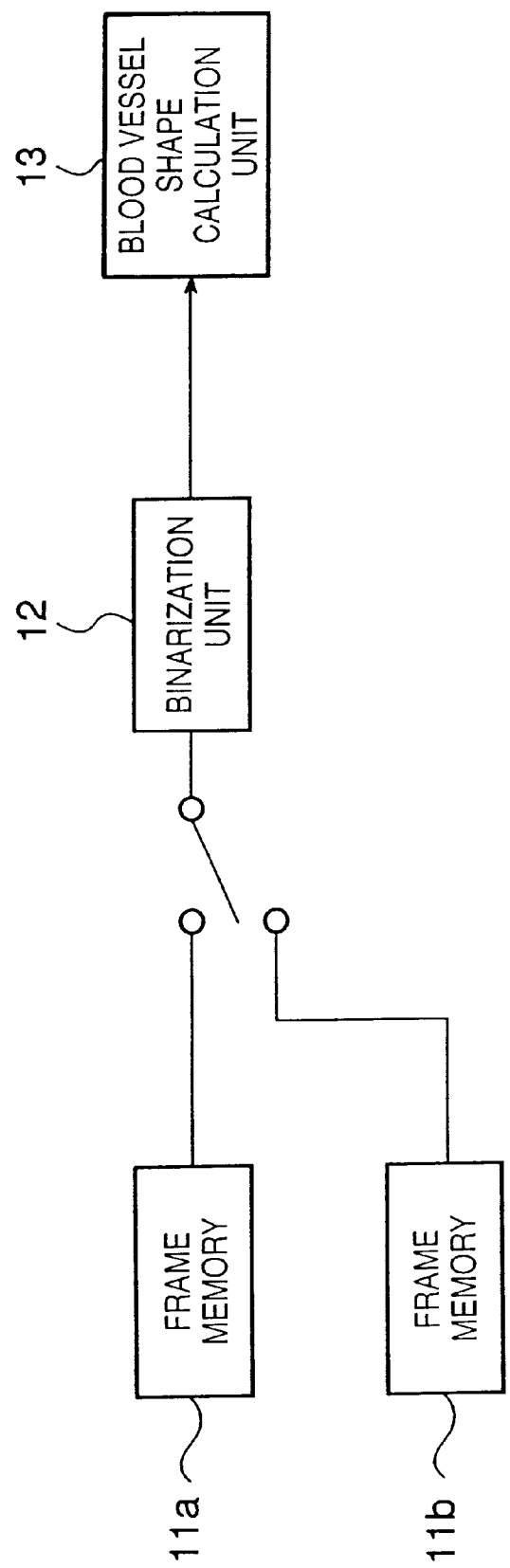
FIG. 3 is a block diagram of a blood vessel cross-sectional area calculation unit.

The resultant tomograms 4a and 4b are transmitted to the blood vessel cross-sectional area calculation unit 5. FIG. 3 is a block diagram showing the arrangement of the blood vessel cross-sectional area calculation unit 5.

The transmitted tomograms are stored in frame memories 11a and 11b. These images are binarized by a binarization unit 12 to extract the blood vessel wall. When a blood vessel is irradiated with an ultrasonic wave, strong reflection occurs at the boundary portion between the blood vessel wall and the interior of the blood vessel. As the blood components in the blood vessel are uniform, a change in acoustic impedance is small, and the reflected wave is weak. When an image is to be reconstructed such that a larger monochrome gradation value is assigned to a reflected wave having a larger magnitude and a smaller monochrome gradation value is assigned to a reflected wave having a small magnitude, the boundary portion between the blood vessel wall and the interior of the blood vessel is expressed by a whitish image, while the interior of the blood vessel is expressed by a blackish image having an a low gradation level. By using this nature, the following processing (binarization) is performed. A given gradation value is defined as a threshold value. A portion having a value equal to or larger than the threshold value is expressed as white, i.e., the maximum gradation value, while a portion having a value smaller than the threshold value is expressed as black, i.e., the minimum gradation value. This binarization is generally performed in the field of image processing.

A blood vessel shape calculation unit 13 calculates the area of the interior of the blood vessel and the blood vessel diameter using the image having the black interior of the blood vessel which is obtained by binarization. The calculated area and diameter are transmitted to the blood flow velocity calculation unit 6 and the pulse wave velocity calculation unit 7. The tomograms can be continuous obtained along the time axis to obtain a time change in sectional shape of the blood vessel.

As indicated by the solid line in FIG. 4, the blood flow velocity calculation unit 6 calculates cross-sectional areas Sa(t) and Sb(t) (measurement data which change along the time axis) of blood vessel sections 14a and 14b by using the ultrasonic transducer groups 4a and 4b and then calculates an average flow velocity v in the sections at points A and B using the calculated cross-sectional areas as follows:

$$v = \frac{\dot{s}_b(t) - \dot{s}_a(t)}{s_b(t) - s_a(t)} L$$

where

L is the distance between points A and B, and

· represents the time differential.

The above equation is valid as follows.

The radial velocity and pressure gradients of an artery can be neglected in the blood flow. In this case, only the axial average velocity is taken into consideration as a flow. Note that a change in cross-sectional area (therefore the radius) of the blood vessel is taken into consideration. This model is called a quasi-one-dimensional model.

Figure 5:
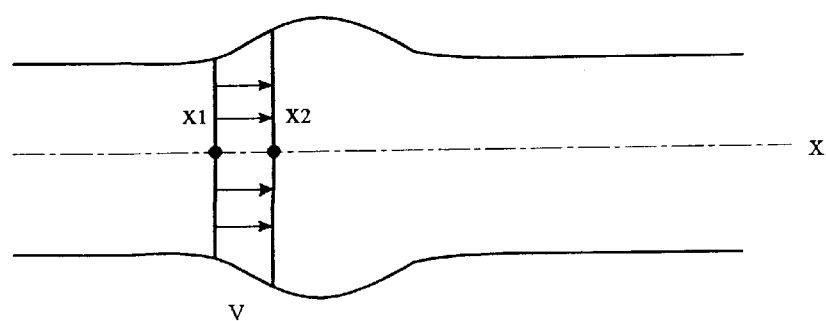
FIG. 5 is a view showing the coordinate system of a quasi-one-dimensional model.

FIG. 5 shows the coordinate system of the quasi-one-dimensional model. The axis of the blood vessel is defined as the x-axis. Let $S(x,t)$ be the cross-sectional area of the blood vessel. The positions of the measurement points (two sections) are given as $x=x1$ and $x=x2$ ($x1<x2$). Position x2 is the downstream point. The position $x=0$ is given as the ejection portion of the heart (but this position may be defined as another arbitrary point).

In a quasi-one-dimensional flow, the following continuity equation holds:

$$\partial S/\partial t + \partial (vS)/\partial x = 0 \quad (1)$$

Equation (1) can be rewritten as follows:

$$\partial (vS)/\partial x = -\partial S/\partial t \quad (2)$$

Equation (2) is integrated for x within the interval $[x, +\infty]$ as follows:

$$\lim_{x \to \infty} v(x, t) = 0$$

($\because$ v is sufficiently small at a sufficient remote position), and the following value is a finite value:

$$\lim_{x \to \infty} s(x, t)$$

The following equations hold:

$$-vs = -\int_x^\infty \frac{\partial s}{\partial t} dx \quad (3)$$

$$\therefore v = \frac{1}{s} \int_x^\infty \frac{\partial s}{\partial t} dx$$

The volume flow rate $Q(x,t)$ is given by the definitions of v and S as follows:

$$Q(x,t) = v(x,t)S(x,t) \quad (4)$$

A substitution of equation (3) into equation (4) yields the following:

$$Q(x, t) = \int_x^\infty \frac{\partial S}{\partial t} dx \quad (5)$$

From equation (5), the flowstream $Q(x_1,t)$ for $x=x_1$ is given as follows:

$$Q(x_1, t) = \int_{x_1}^\infty \frac{\partial s}{\partial t} dx \quad (6)$$

$$= \int_{x_1}^{x_2} \frac{\partial s}{\partial t} dx + \int_{x_2}^\infty \frac{\partial s}{\partial t} dx$$

Assume that T is given as a time shorter than the pulsation period, and a time to be measured is an interval $[0,T]$. In the flow of interest, the heat beat can be regarded as a single wave during an interval from a given beat to the next beat. In the following conditions:

$$x_2 \leq x < \infty, \ 0 \leq t \leq T$$

S does not change along the time axis because the pulse wave does not reach and is a function of only x. The second term of equation (5) can be rewritten as follows:

$$\int_{x_2}^\infty \frac{\partial S}{\partial t} dx = 0 \quad (7)$$

Therefore, $$Q(x_1, t) = \int_{x_1}^{x_2} \frac{\partial S}{\partial t} dx \quad (8)$$

Since the interval $[x_1, x_2]$ is very short, S monotonically increases or decreases for x within the interval $[x_1, x_2]$, so that the following linear approximation can be made:

$$S(x,t) = (x+a)f(t) \quad (9)$$

where a is a constant

Therefore, $$\frac{\partial S}{\partial t} = (x+a)\dot{f}(t) \quad (10)$$

A substitution of equation (10) into equation (8) yields the following:

$$Q(x_1, t) = \dot{f}(t) \int_{x_1}^{x_2} (x+a) dx \quad (11)$$

$$= \dot{f}(t) \left[ \frac{1}{2} x^2 + ax \right]_{x_1}^{x_2}$$

$$= \dot{f}(t)(x_2 - x_1) \left\{ \frac{1}{2} (x_1 + x_2) + a \right\}$$

From equation (4), the following equation can be derived:

$$v(x_1,t) = Q(x_1,t)/S(x_1,t)$$

Substitutions of equations (9) and (11) into the above equation yield the following:

$$v(x_1, t) = \frac{\dot{f}(t)(x_2 - x_1) \frac{1}{2}(x_1 + x_2 + 2a)}{(x_1 + a)f(t)} \quad (12)$$

Since $x_2 - x_1$ is much smaller than $x_1$ and $x_2$, the following equation can be approximated:

$$x_1 + x_2 + 2a \approx 2(x_1 + a) \quad (13)$$

equation (12) can be rewritten as follows:

$$v(x_1, t) = \frac{\dot{f}(t)}{f(t)} (x_2 - x_1) \quad (14)$$

Since the following equation holds:

$$L = x_2 - x_1 \quad (15)$$

the following equation holds:

$$v(x_1, t) = \frac{\dot{f}(t)}{f(t)} L \quad (16)$$

From equation (9), the following equations hold:

$$S(x_1,t) = (x_1 + a)f(t) \quad (17)$$

$$S(x_2,t) = (x_2 + a)f(t) \quad (18)$$

and the difference between equations (17) and (18) is calculated as follows:

$$S(x_2,t) - S(x_1,t) = f(t)L \quad (19)$$

Since the following equations hold:

$$S(x_1,t) = Sa(t) \quad (20)$$

$$S(x_2,t) = Sb(t) \quad (21)$$

substitutions of equations (20) and (21) yield the following:

$$Sb(t) - Sa(t) = f(t)L \quad (22)$$

The right- and left-hand sides of equation (22) are differentiated as follows:

$$\dot{S}_b(t) - \dot{S}_a(t) = \dot{f}(t)L \quad (23)$$

Equation (16) can be rewritten using equations (22) and (23):

$$v(x_1, t) = \frac{\dot{S}_b(t) - \dot{S}_a(t)}{S_b(t) - S_a(t)} L \quad (24)$$

The average flow velocity at $x=x_1$ can be obtained by equation (24). The flowstream $Q(x_1,t)$ can be defined from equation (4) as follows:

$$Q(x_1, t) = S_a(t) \frac{\dot{S}_b(t) - \dot{S}_a(t)}{S_b(t) - S_a(t)} L$$

Figure 4:
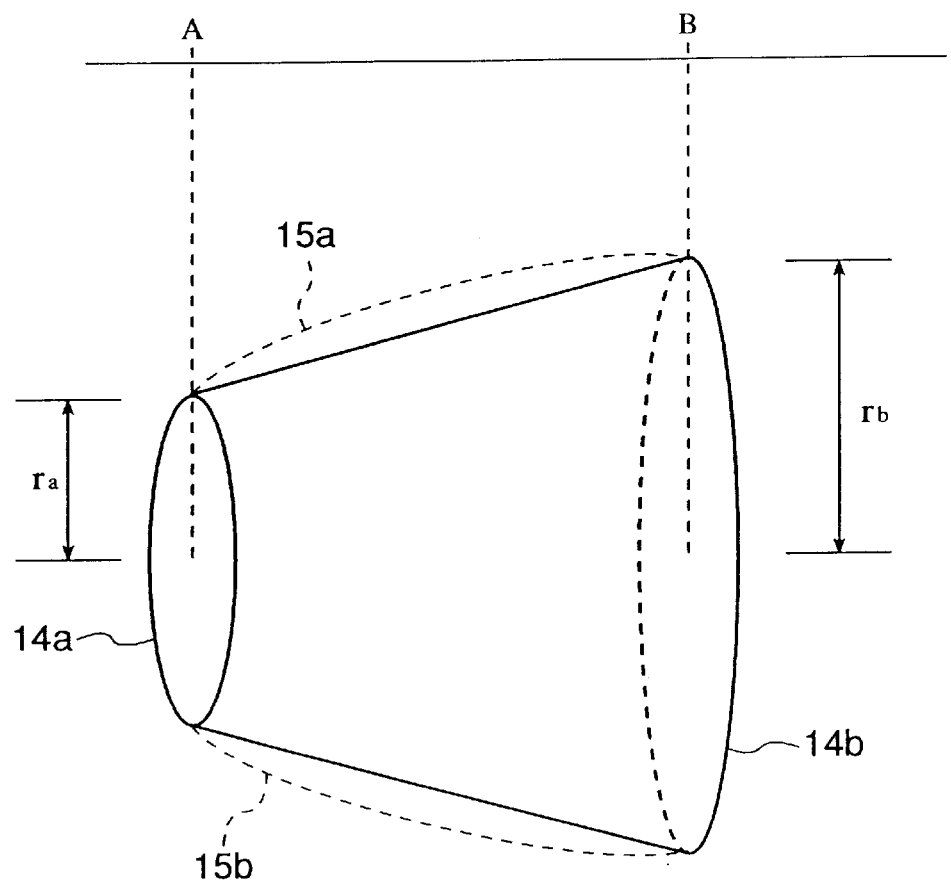
FIG. 4 is an enlarged view of part of a blood vessel.

The actual blood vessel as shown in FIG. 4 may take the shapes indicated by dotted lines 15a and 15b. As an improvement for reducing linear approximation errors, the following methods can be practiced: a method of shortening the distance between the two sections; a method of arranging the ultrasonic transducers in a matrix array to obtain an accurate value; and a method of performing integration by defining side portions with actual curves, i.e., the curves matching the dotted lines. These methods are apparently incorporated within the scope of the present invention.

The pulse wave velocity calculation unit 7 divides the distance between points A and B by a time delay τ (phase difference) of a time change in cross-sectional areas between points A and B, thereby calculating the pulse wave velocity C0 as follows:

$$C0 = L/\tau$$

The blood pressure change calculation unit 8 substitutes the transmitted flow velocity and the pulse wave velocity into the following theoretical expression:

$$P - P0 = \rho C0 v + (1/8)\rho v^2$$

This expression is described in the following reference (Motoaki Sugawara, Yasuhisa Sakurai, et. al., "Nonlinear Theory of pulse wave in arteries", Japanese Journal of Medical Electronics and Biological Engineering, Vol. 11, No. 3, 180–189, 1973).

The above processing allows the blood pressure calculation unit 10 to continuously calculate the blood pressures on the basis of the blood pressure values at time phases measured by the reference pressure measurement unit 9. This reference pressure can be measured by, e.g., a method of setting the reference pressure by measuring the minimum blood pressure using a manchette type automatic sphygmomanometer (one-point measurement of measuring the blood pressure once within a given time) in advance. The reference pressure is not limited to the minimum blood pressure. Any setting method can be used if a pressure value and a blood pressure change calculation unit output are simultaneously obtained.

The calculated blood pressure value can be output to a display device such as a blood pressure display liquid crystal monitor, a recording memory medium, a printer, or the like, as needed, in accordance with the request of an operator.

In the above embodiment, the signals obtained by allowing the ultrasonic transducer groups 4a and 4b to receive the ultrasonic waves reflected in the living body are converted into an image signal, and the signal is then binarized. However, the reception signals output from the ultrasonic transducer groups 4a and 4b may be logarithmically amplified and detected, and the detected signal may be binarized.

(Second Embodiment)

In the first embodiment, the blood vessel cross-sectional area calculation unit 5 performs binarization using a given fixed value to extract a blood vessel image as a binary image. The method of calculating the blood vessel cross-sectional area is not limited to this.

Figure 6:
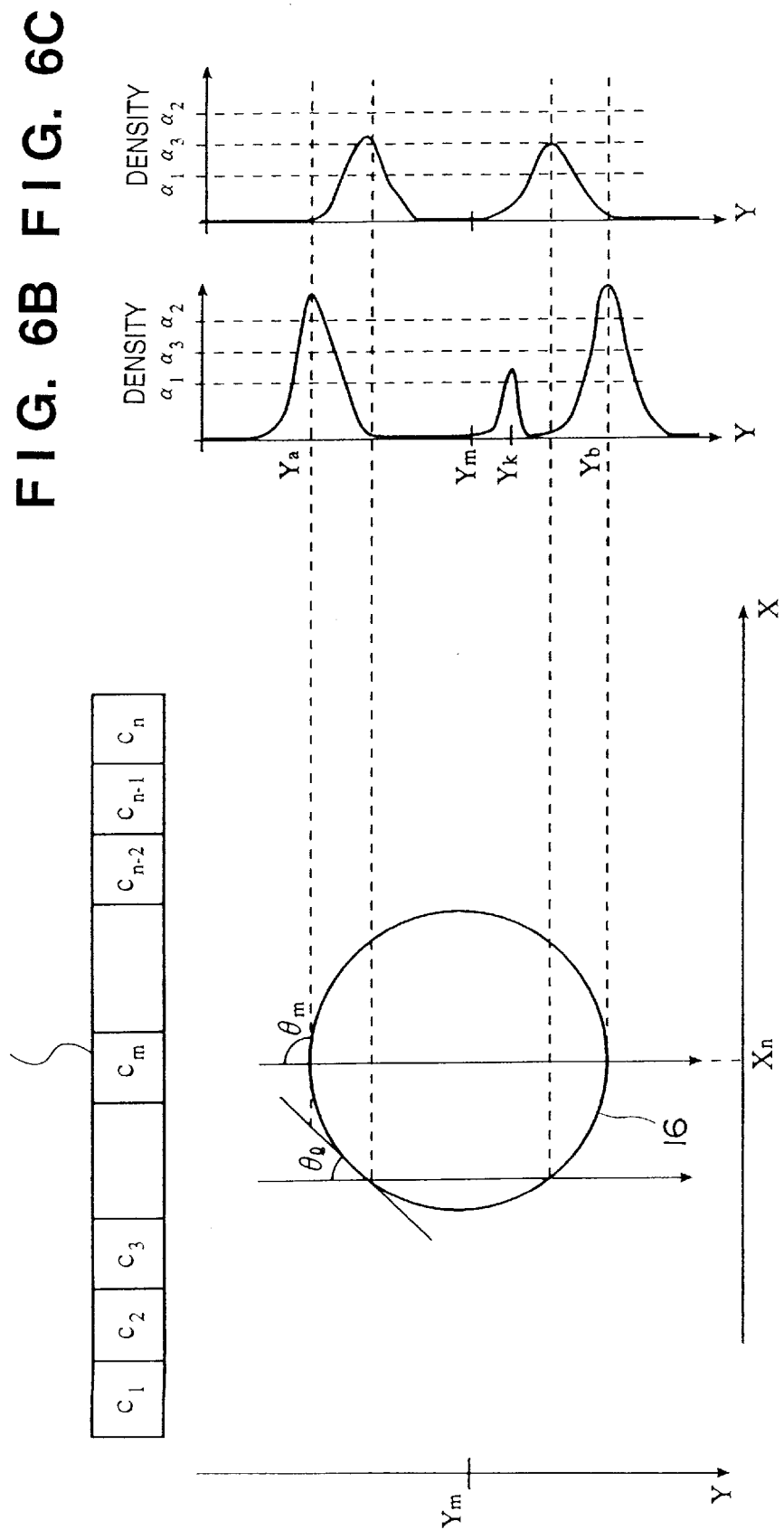
FIGS. 6A to 6C are views showing the relationship between the ultrasonic wave signal and the blood vessel wall surface.

FIGS. 6A to 6C show the relationship between the ultrasonic signal and a wall surface 16 of a blood vessel. As shown in FIG. 6A, an ultrasonic wave emitted from a Cmth ultrasonic transducer located at a position right above the center of the blood vessel is incident on the blood vessel perpendicularly to the tangential line of the blood vessel wall. A reflected wave detected by this vibrator Cm has a large magnitude. An ultrasonic wave emitted by a vibrator remote from the position right above the blood vessel is incident on the blood vessel obliquely from the tangential line of the blood vessel wall. A reflected wave detected by the remote vibrator has a smaller magnitude than that of the vibrator Cm. In beam forming using a plurality of vibrators, a reflected wave has a large magnitude when the central axis of the ultrasonic beam is closer to the center of the blood vessel; otherwise, the reflected wave has a smaller magnitude.

Assume that the intensity of the reflected wave detected by the Cmth ultrasonic transducer located at the position right above the center of the blood vessel has a shape shown in FIG. 6B. Portions corresponding to the blood vessel wall portions are presented by Ya and Yb, and a portion Yk represents noise. In this case, to properly extract the blood wall portions, a threshold level is preferably set at about $\alpha 2$, i.e., a level higher than the noise peak and lower than the blood vessel wall peak.

Since the ultrasonic transducer in FIG. 6C is not located at the position right above the center of the blood vessel, the intensity of the wave reflected by the blood vessel wall portion is weak and does not reach the threshold value $\alpha 2$. The threshold value must fall within the range of $\alpha 1$ to $\alpha 3$, resulting in inconvenience. If noise is present, the blood vessel wall may not be properly extracted in binarization using the fixed threshold value.

To solve this problem, this embodiment employs a method of changing the threshold value in accordance with an incident angle of the ultrasonic wave with respect to the tangential line of the blood vessel wall.

Figure 7:
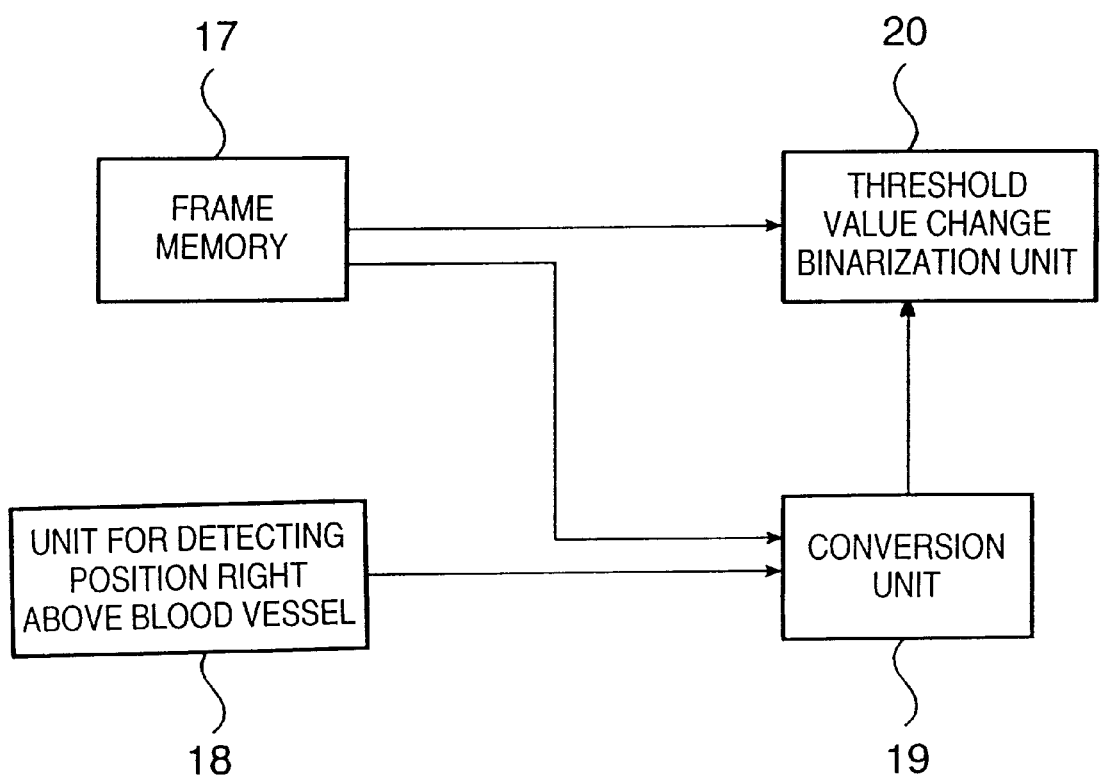
FIG. 7 is a block diagram showing the schematic arrangement of a blood vessel cross-sectional area calculation unit according to the second embodiment.

FIG. 7 is a block diagram showing the schematic arrangement of the blood vessel cross-sectional area calculation unit of this embodiment. A unit 18 for detecting the position right above the blood vessel of interest detects a specific vibrator which is located at the position right above this vessel.

FIG. 8 shows the arrangement of the unit for detecting the position right above the blood vessel. An image obtained by ultrasonic transducer group 3c in FIG. 6A is displayed on a display monitor 21. A marker 22 indicating a specific screen position for an image portion obtained by a vibrator located at the center or a position near the center of the ultrasonic transducer group 3c is displayed on the monitor. The operator moves the probe to match the center of the blood vessel image with the marker 22. After the probe position is adjusted such that a blood vessel image 23a shifted from the center comes to a blood vessel image 23b matching the center of the marker, the operator presses a detection end confirmation button, and a measurement is started.

On the basis of an address of a frame memory 17, a conversion unit 19 calculates that data read out from the frame memory 17 is data obtained by which one of the vibrators of the ultrasonic transducer group. The conversion unit 19 transmits the calculation result to a threshold value change binarization unit 20. The threshold value change binarization unit 20 changes the threshold value and outputs a binary threshold value on the basis of the data output from the above conversion unit.

The threshold value set by the threshold value change binarization unit 20 is not necessarily determined by only the incident angle of the ultrasonic signal incident on the blood vessel wall. In practice, threshold value setting can change depending on the measurement conditions and patients. Appropriate correction items for changes in threshold value do not depart from the scope of the present invention.

A blood vessel cross-sectional area S and a blood vessel inner radius r can be obtained from the extracted blood vessel wall, or a blood vessel state can be obtained by a time change in blood vessel wall.

Figure 9A:
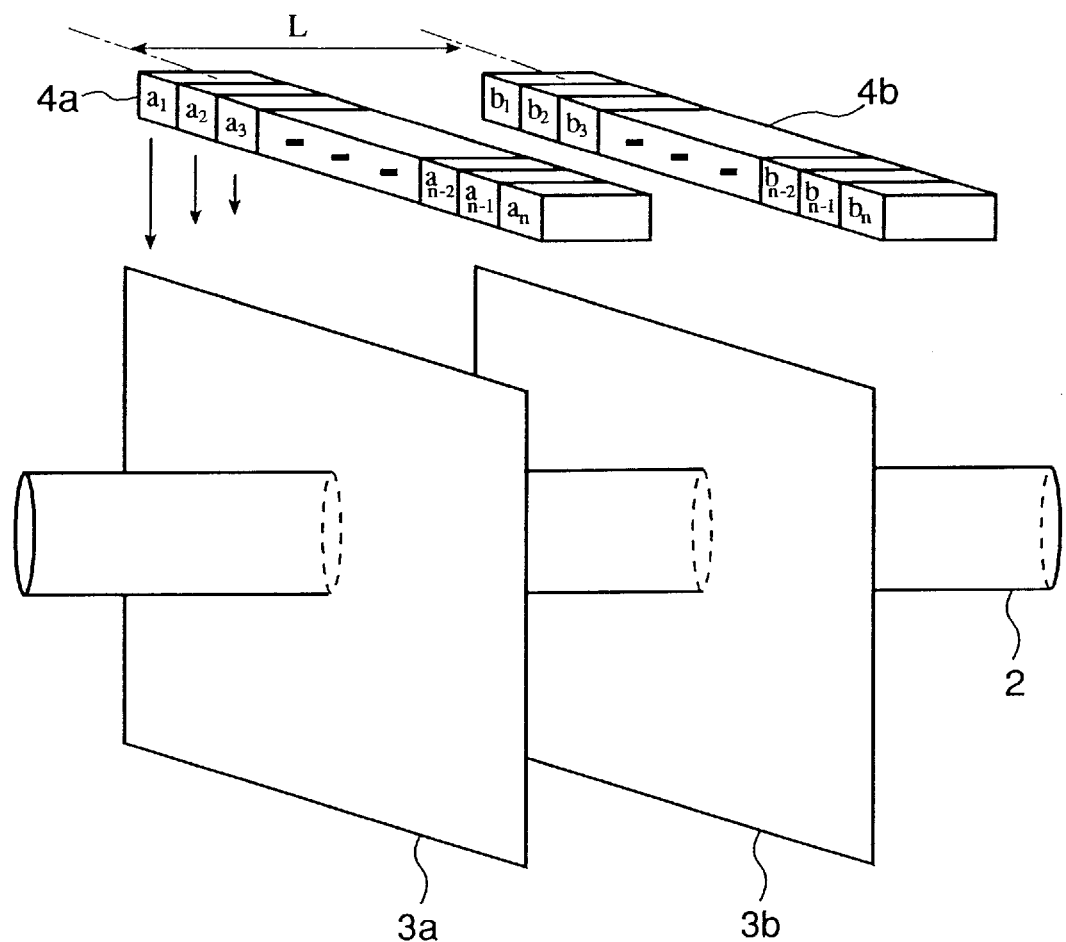
FIGS. 9A and 9B are views showing an arrangement for obtaining a pulse wave propagation velocity.
Figure 9B:
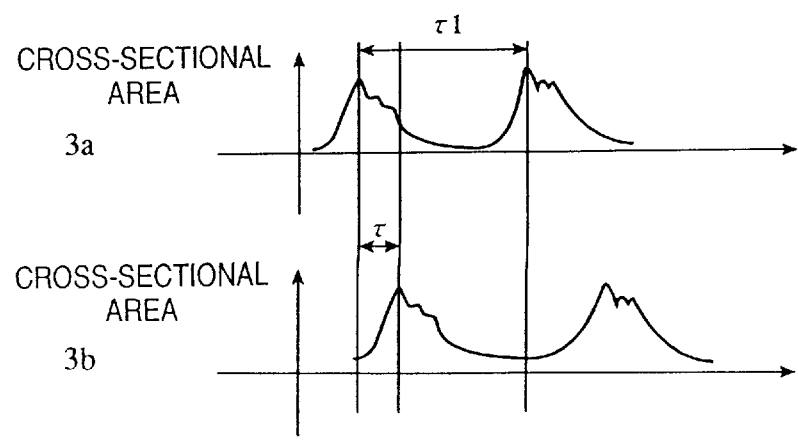

A method of reflecting the Young's modulus and calculating a pulse wave propagation velocity regarded as an index of arteriosclerosis will be described below. FIG. 9A shows an arrangement for obtaining a pulse wave propagation velocity, and FIG. 9B shows the resultant waveforms. Ultrasonic transducer groups are placed above an artery and spaced apart from each other by a distance L. A cross-sectional area is obtained from tomograms obtained from the ultrasonic transducer groups in accordance with the above technique. As shown in FIG. 9B, the resultant waves reflect the pulsation. The pulse wave velocity C is obtained by $C=L/\tau$ where $\tau$ is the time delay (phase difference) of changes in cross-sectional areas in two tomograms 3a and 3b. The pulse wave velocity is generally obtained by the time difference between the carotid wave and the hip artery wave and reflects the degree of arteriosclerosis of all the arteries present between the carotid and the femoral artery. According to the method of the present invention, a local pulse wave propagation velocity can be measured. Therefore, detailed diagnosis can be performed to specify a specific progressed arteriosclerotic portion.

A pulse rate RR converted per minute can be obtained using a conversion formula $RR=60/\tau 1$ using a period $\tau 1$ of a change in cross-sectional area of the tomogram 3a in FIG. 9B.

The volume flow of blood and the average flow velocity within the section can be obtained from the two tomograms 3a and 3b. The method of obtaining these values has already been described in the first embodiment.

In combination with the blood pressure measurement technique, the elasticity of the blood vessel can be directly obtained. Measurements effective for evaluating the degree of arteriosclerosis are allowed. A pressure elasticity Ep is defined as the index of the degree of arteriosclerosis as follows:

$$Ep=\Delta P/(\Delta r/r)$$

This index is obtained by measuring the pressure and blood vessel diameter using an intravascular catheter in Japanese Patent Laid-Open No. 4-329938. The method of this embodiment, however, allows a noninvasive measurement.

In addition to the pulse rate, the pulse wave velocity, and the pressure elasticity, various other cardiovascular data such as the thickness of the blood vessel wall and the pulsation rate of the blood vessel wall can be obtained from the extracted time changes of cross-sectional areas of the blood vessel wall portions. All these data are apparently incorporated in the category of the present invention.

(Third Embodiment)

The second embodiment has exemplified the method of manually detecting the position right above the center of the blood vessel. It is also possible to specify the position right above the blood vessel in accordance with another method. The third embodiment will exemplify a method of detecting a position right above a blood vessel using a pressure-sensitive element.

FIG. 10 is a view showing the schematic arrangement of a pressure-sensitive element group for obtaining the center of a blood vessel 2. The pressure-sensitive element group 31 is pressed using a pressing portion such as a manchette to pressurize a blood vessel, thereby flatten the blood vessel, as shown in FIG. 10. A pressure value is transmitted to the pressure-sensitive element group 31. A portion representing the maximum transmitted pressure is defined as a position right above the blood vessel.

The portion representing the maximum transmitted pressure is defined as the position right above the blood vessel. However, this portion changes depending on the pressurizing method, the pressurizing strength, and the position of a blood vessel. The method of determining the position right above the blood vessel can be arbitrarily improved.

Figure 11:
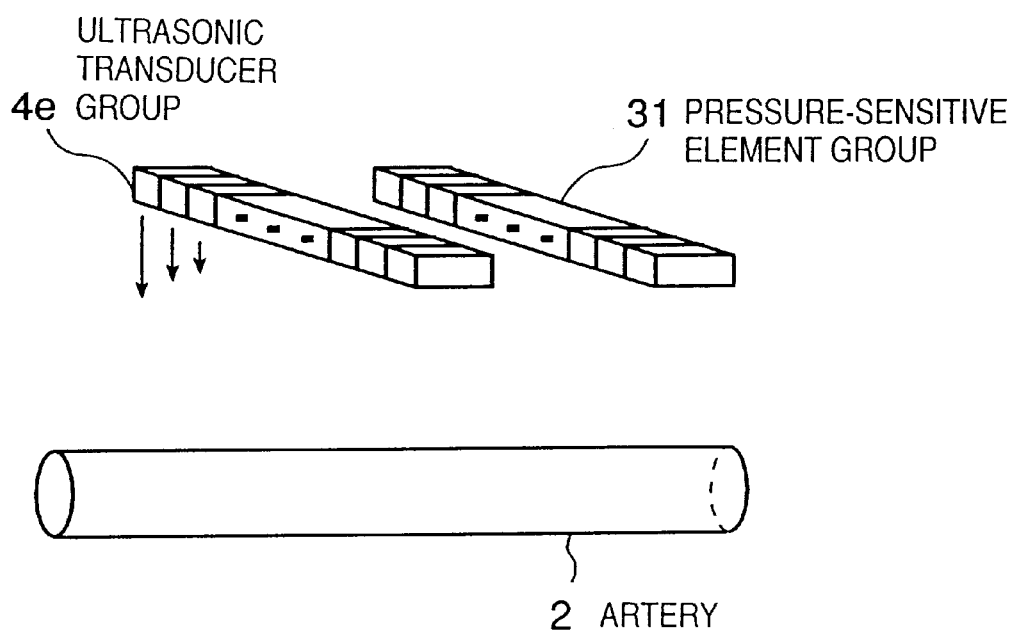
FIG. 11 is a perspective view showing an arrangement of a means for detecting a position right above a blood vessel.

FIG. 11 is a view showing the arrangement of a means for detecting the position right above the blood vessel. An ultrasonic transducer group 4e is arranged parallel to a pressure-sensitive element group 31. Prior to measuring a blood vessel image, the pressure-sensitive element group 31 is pressed against a patient at an appropriate pressure to determine which one of the pressure elements of the pressure-sensitive element group 31 is located right above the blood vessel of interest on the basis of the pressure wave. In this determination, the pressure waves of the respective pressure elements which change over time in accordance with the pulsation of the blood vessel are compared with each other, and the pressure-sensitive element generating the maximum output is determined as the one located right abot is possible to release the pressure from the blood vessel in order not to flatten the blood vessel.

According to the second embodiment, the threshold value is changed in accordance with the incident angle of the ultrasonic wave. However, the present invention is not limited to the case in which the threshold value is determined by only the incident angle (e.g., the proportional relationship between the incident angle and the sine value). When it is difficult to sequentially calculate the incident angles, due to the structural complexity of the measurement equipment, for ultrasonic images obtained from the respective vibrators, the following method can be employed. That is, an image portion obtained by an ultrasonic signal received by the ultrasonic transducer located right above the blood vessel is set to have zero incident angle. The threshold value is changed using an arbitrary waveform such as a linear or curved waveform when remote from this vibrator. In other words, a simple method using only incident angle information at one or several positions is also incorporated in the scope of the present invention.

Figure 12A:
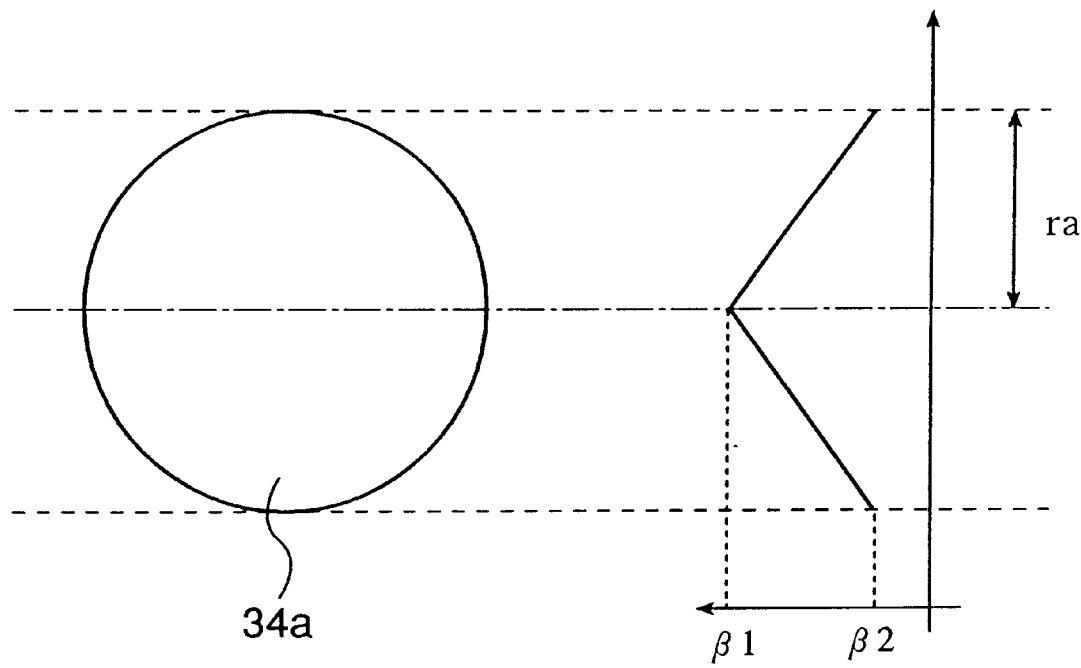
FIGS. 12A and 12B are views showing an example of setting a threshold value.
Figure 12B:
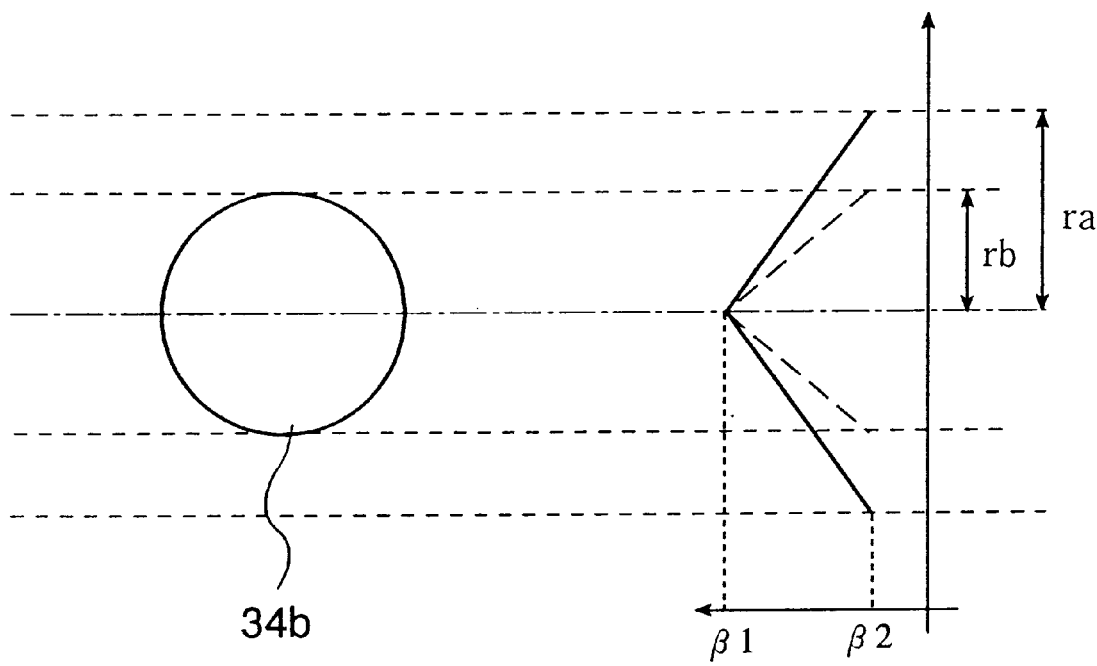

FIGS. 12A and 12B are views showing an example of setting the threshold values. In FIG. 12A, a threshold value for a portion located right above the blood vessel is given as β1 to linearly change the threshold value. A threshold value remote from the position right above the blood vessel by ra is set to have a threshold value β2. Even if a single blood vessel has pulsation, different threshold values are set in the diastole and systole. When the blood vessel is kept dilated as indicated by reference numeral 34a in FIG. 12B, the threshold value is changed depending on pulsation, as indicated by the solid line. When the blood vessel is kept constricted as indicated by reference numeral 34b, the threshold value is changed depending on pulsation, as indicated by the dotted line. More specifically, there is employed a method of arranging the vasodilation and vasoconstriction detection units for detecting the diastole and systole and changing the threshold values in accordance with the data from these detection units.

Alternatively, the threshold value may be changed by a line or curve depending on the incident angle as described above, and the entire change curve representing the threshold value line or curve may be vertically translated by a volume control or the like. The volume control may be adjusted so that the blood vessel wall is most clearly observed while viewing the binary tomogram on the screen.

As described above, when an appropriate threshold value in accordance with the blood vessel state, the arterial wall can be extracted, and various kinds of cardiovascular information can be measured using the extracted arterial wall image.

The apparatus of the present invention can be arbitrarily used as part of another apparatus within the spirit and scope of the present invention. For example, the apparatus of the present invention is synchronized with an ultrasonic diagnosis apparatus to superpose the extracted blood vessel wall on the ultrasonic image and display the resultant image on a monitor, and output the resultant values on the screen or print them on paper. These modifications are also incorporated within the scope of the present invention.

As has been described above, according to the present invention, the blood pressure can be continuously and noninvasively measured using a theoretical expression in consideration of the blood vessel wall movement by pulsation of the blood vessel wall.

There can be provided a cardiovascular information measurement system capable of noninvasively measuring cardiovascular indices such as a blood vessel state and a blood flow by using the arrangement capable of extracting a blood vessel wall portion from the ultrasonic tomograms.

The present invention is not limited to the above embodiments and various changes and modifications can be made within the spirit and scope of the present invention. Therefore, to apprise the public of the scope of the present invention the following claims are made.

What is claimed is:

1. A cardiovascular information measurement system characterized by comprising:

sectional shape detection means for simultaneously detecting sectional shapes of at least two arterial portions;

cross-sectional area calculation means for calculating cross-sectional areas of the two arterial portions on the basis of the sectional shapes detected by said sectional shape detection means;

flow velocity calculation means for calculating an average blood flow velocity in an artery on the basis of the cross-sectional areas calculated by said cross-sectional area calculation means;

pulse wave velocity calculation means for calculating a pulse wave propagation velocity between the two arterial portions in accordance with time changes in the sectional shapes of the two arterial portions which are detected by said sectional shape detection means;

relative blood pressure calculation means for calculating a relative blood pressure value to a reference blood pressure value obtained in a specific time phase, on the basis of the blood flow velocity calculated by said flow velocity calculation means and the pulse wave velocity calculated by said pulse wave velocity calculation means; and absolute blood pressure calculation means for calculating an absolute blood pressure value on the basis of the relative blood pressure value and the reference blood pressure value obtained in the specific time phase and measured in advance.

2. The system according to claim 1, characterized in that said flow velocity calculation means calculates an average blood flow velocity of a portion surrounded by the two arterial portions and a blood vessel wall in accordance with the cross-sectional areas of the two arterial portions, their time differential values, and a distance between the sections of the two arterial portions.

3. The system according to claim 1, characterized in that said sectional shape detection means comprises ultrasonic emission means for emitting an ultrasonic wave toward the artery, ultrasonic detection means for detecting an ultrasonic wave reflected in a living body, and binarization means for binarizing an output signal from said ultrasonic detection means using an appropriate threshold value as a reference in order to extract the sectional shape of the arterial wall.

4. The system according to claim 3, characterized in that said binarization means comprises threshold value correction means for correcting the threshold value by vasodilation and vasoconstriction.

5. The system according to claim 3, characterized in that said binarization means comprises means for detecting a position right above the center of the artery.

6. The system according to claim 3, characterized in that said ultrasonic emission means and said ultrasonic detection means comprise a plurality of ultrasonic emission means and a plurality of ultrasonic detection means, and said system further comprises pulse wave velocity measurement means for measuring a pulse wave propagation velocity in accordance with a phase difference of changes in sectional shapes of a plurality of arterial walls which are obtained by said plurality of ultrasonic detection means.

7. The system according to claim 3, characterized in that said sectional shape detection means further comprises conversion means for converting an output from said ultrasonic detection means into an image signal.

8. The system according to claim 7, characterized in that said binarization means binarizes the converted image signal using an appropriate image density value as a threshold value after said conversion means converts the output signal from said ultrasonic detection means into the image signal.

9. The system according to claim 3, characterized in that said binarization means comprises setting means for setting the threshold value in accordance with an angle formed between an ultrasonic incident direction and the arterial wall.

10. The system according to claim 9, characterized in that said binarization means further comprises arithmetic means for calculating an angle between an ultrasonic wave incident direction and the arterial wall on the basis of the cross-sectional area detected by said sectional shape detection means and the ultrasonic wave incident direction.

11. A cardiovascular information measurement system characterized by comprising:

ultrasonic emission means for emitting an ultrasonic wave toward a blood vessel;

ultrasonic wave detection means for detecting an ultrasonic wave reflected in a living body;

binarization means for setting an appropriate threshold value in accordance with an angle between an incident direction of the ultrasonic wave and a blood vessel wall and binarizing an output signal from said ultrasonic detection means; and index calculation means for calculating a cardiovascular index on the basis of blood vessel sectional shape information obtained from information binarized by said binarization means.

12. The system according to claim 11, characterized in that said binarization means comprises threshold value correction means for correcting the threshold value by vasodilation and vasoconstriction.

13. The system according to claim 11, characterized in that said binarization means comprises means for detecting a position right above the center of the blood vessel.

14. The system according to claim 13, characterized in that said means for detecting the position right above the center of the blood vessel comprises a plurality of pressure-sensitive elements bought into contact with a skin surface near the position right above the blood vessel while crossing the blood vessel, and a processing unit for detecting the position right above the blood vessel in accordance with pulse waves detected by said pressure-sensitive elements.

15. The system according to claim 14, characterized in that said plurality of pressure-sensitive elements are arranged substantially parallel to a plurality of ultrasonic transducers constituting said ultrasonic detection means.

16. The system according to claim 11, characterized in that said ultrasonic emission means and said ultrasonic detection means comprise a plurality of ultrasonic emission means and a plurality of ultrasonic detection means, and said system further comprises pulse wave velocity measurement means for measuring a pulse wave propagation velocity in accordance with a phase difference of changes in sectional shapes of a plurality of blood vessel walls which are obtained by said plurality of ultrasonic detection means.

17. The system according to claim 11, characterized in that said index calculation means comprises pulse wave measurement means for measuring a pulse wave on the basis of a change in blood vessel diameter or section.

18. The system according to claim 11, characterized in that said index calculation means comprises displacement detection means for detecting a change in blood vessel diameter or section, pressure measurement means for detecting a pressure acting on the wall surface of the blood vessel, and dynamic property calculation means for calculating a dynamic viscoelasticity of the blood vessel on the basis of results obtained from said displacement detection means and said pressure measurement means.

* * * * *

UNITED STATES PATENT AND TRADEMARK OFFICE
CERTIFICATE OF CORRECTION

PATENT NO.    : 6,176,832 B1
DATED         : January 23, 2001
INVENTOR(S)   : Yoshiyuki Habu, et al.

It is certified that error appears in the above-identified patent and that said Letters Patent is hereby corrected as shown below:

7th Listed Reference Cited is corrected to:
Item [56], Reference Cited U. S. PATENT DOCUMENTS 5,588,435     12/1996     Weng et al.

<u>Column 4,</u>
Line 26, "$3b$" is changed to -- $4b$ --.
Line 27, "$3a$" is changed to -- $4a$ --.

Signed and Sealed this

Thirtieth Day of October, 2001

*Attest:*

*Attesting Officer*

NICHOLAS P. GODICI
*Acting Director of the United States Patent and Trademark Office*